Figure 1:
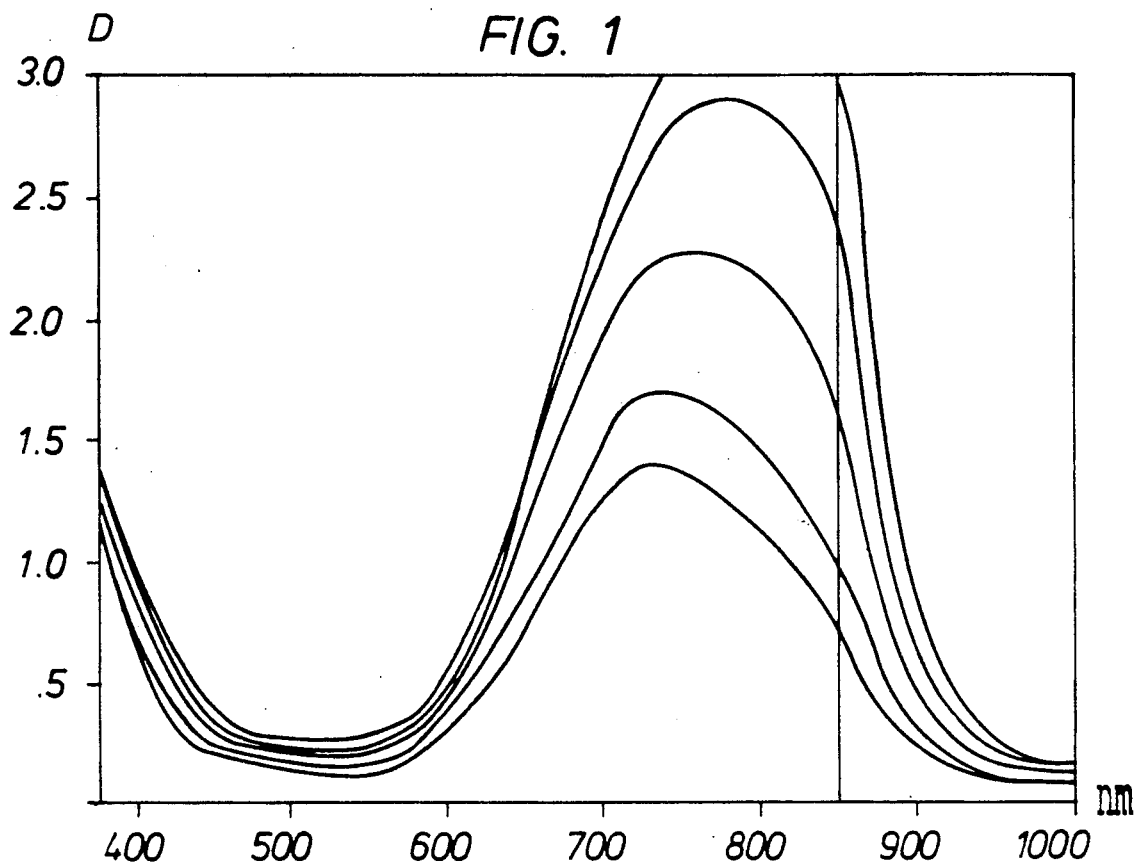

United States Patent [19]

Olbrechts et al.

[11] Patent Number: 5,030,544
[45] Date of Patent: * Jul. 9, 1991

[54] PHOTOGRAPHIC ELEMENTS COMPRISING THIAZOLYL COUPLERS CAPABLE OF FORMING INFRARED-ABSORBING DYES FOR INTEGRAL SOUND TRACK

[75] Inventors: Henri F. Olbrechts, Brasschaat; Raphaël K. Van Poucke, Berchem; Van den Sande, Belsele, all of Belgium

[73] Assignee: Agfa-Gevaert, N.V., Mortsel, Belgium

[*] Notice: The portion of the term of this patent subsequent to Jun. 13, 2006 has been disclaimed.

[21] Appl. No.: 780,585

[22] Filed: Sep. 26, 1985

[30] Foreign Application Priority Data

Sep. 28, 1984 [BE] Belgium .................. 84201385

[51] Int. Cl.$^5$ ................................. G03C 7/24
[52] U.S. Cl. .................... 430/140; 430/505; 430/552; 430/553; 430/546
[58] Field of Search ........... 430/552, 553, 558, 505, 430/140, 546

[56] References Cited

U.S. PATENT DOCUMENTS

| | | | |
|---|---|---|---|
| 2,266,452 | 12/1941 | Vittum et al. | 430/552 X |
| 2,373,821 | 4/1945 | Frömlich et al. | 430/558 X |
| 3,458,315 | 7/1969 | Loria | 430/558 X |
| 3,476,563 | 11/1969 | Loria | 430/558 X |
| 4,178,183 | 12/1979 | Ciurca, Sr. et al. | 430/140 X |
| 4,208,210 | 6/1980 | Sakai et al. | 430/140 |
| 4,839,267 | 6/1989 | Monbaliv et al. | 430/546 |

FOREIGN PATENT DOCUMENTS

| | | | |
|---|---|---|---|
| 717931 | 9/1965 | Canada | 430/552 |
| 519208 | 3/1940 | United Kingdom | 430/552 |

Primary Examiner—Paul R. Michl
Assistant Examiner—Janet C. Baxter
Attorney, Agent, or Firm—Breiner & Breiner

[57] ABSTRACT

Color photographic motion picture elements adapted to form a multicolor photographic dye image and an integral, infrared-absorbing, dye sound track and comprising 1-hydroxy-2-N-(5-alkyl-thiazol-2-yl)- naphthamide couplers that are capable of forming quinone imine dyes absorbing infrared radiation in the spectral range from about 600 to about 1000 nm by reaction with an oxidized aromatic primary amino developing agent, the thiazol-2-yl group of said naphthamide couplers bearing a 4-para-$C_1$-$C_4$alkoxyphenyl group or a 4-para-$C_1$-$C_4$alkylphenyl group, the hydrogen atoms of said $C_1$-$C_4$alkoxy or $C_1$-$C_4$alkyl being unsubstituted or at least one of them having been substituted by a halogen atom.

8 Claims, 6 Drawing Sheets

PHOTOGRAPHIC ELEMENTS COMPRISING THIAZOLYL COUPLERS CAPABLE OF FORMING INFRARED-ABSORBING DYES FOR INTEGRAL SOUND TRACK

The present invention relates to novel couplers capable of forming infrared-absorbing dyes, more particularly to couplers capable of forming integral, infrared-absorbing, dye sound tracks in colour photographic motion picture elements, to photographic colour elements comprising such couplers, and to materials comprising such infrared-absorbing dyes.

The photographic image as well as the sound track image in black-and-white motion picture projection films are known to consist of silver usually, the sound information in the sound track being present in the form of periodical variations in density or of periodical variations in the ratio between areas that are completely dark and areas that are fully bright. This sound information can be read optically by a photocell detecting infrared radiation that has been modulated by passing through these variations in density or in area. The photocells customarily used for this purpose are i.a. the S-1 photocells, which have a maximum sensitivity in the infrared region of the spectrum, more particularly in the infrared region from about 750 to about 850 nm, in which region silver absorbs uniformly.

Although in sound tracks of colour motion picture projection films silver has been used customarily, the application of silver therein requires special selective treatments including a separate development of the sound track portion. To avoid such special selective treatments attempts have been made to use dyes instead of silver for the sound tracks of colour motion picture projection films. This allows the formation of both a dye image and a dye sound track during the same and only colour development step. The dye that builds up the sound track is a quinone imine coupling product that should have peak absorption in the infrared region where the photocells, e.g. the S-1 photocells, are sensitive, namely from about 750 to about 850 nm.

Infrared-absorbing dyes that can be used at least partially in integral dye sound tracks have been disclosed in U.S. Pat. No. 2,266,452, U.S. Pat. No. 2,373,821, JP PU 59,838, UK P 1,424,454, U.S. Pat. No. 3,458,315, U.S. Pat. No. 3,476,563, UK P 519,208, in Research Disclosure N°13460 of June 1975, N°15125 of November 1976, and N°18732 of November 1979.

U.S. Pat. No. 4,178,183 teaches the use of 1-hydroxy-2-N-(4-phenyl-5-ballasted-thiazol-2-yl)-naphthamide couplers for forming integral, infrared-absorbing, dye sound tracks in colour photographic motion picture elements.

However, the absorption peaks of the infrared-absorbing dyes hitherto used for integral dye sound tracks are not broad enough and are insufficiently bathochromic. Their peak absorption usually lies between 800 and 820 nm. In these circumstances silver is still needed at least partially to guarantee sufficient absorption in the sensitivity range of the S-1 photocells and to ensure sufficient density. Moreover, the use of these dyes gives rise to a loss in output of the sound track.

It is therefore an object of the present invention to provide 2- or 4-equivalent couplers that are capable of forming dyes that have enhanced infrared peak absorption, have a broadened more bathochromic absorption range that encompasses the sensitivity range of the S-1 photocells, and are not subject to loss in output of the sound track.

It is another object of the present invention to provide colour photographic motion picture elements comprising such couplers that are capable of forming infrared-absorbing dyes for integral dye sound tracks without requiring special selective treatment as above referred to, and which have sufficient density in the absence of silver and show no significant loss in output of the sound track.

It is a further object of the present invention to provide dyes that have a high infrared peak absorption and offer a broadened more bathochromic absorption range than the known infrared-absorbing dyes.

Other objects of the present invention will become apparent from the disclosure herein.

The above objects are accomplished by the use, in colour photographic motion picture elements, adapted to form a multicolour photographic dye image and an integral, infrared-absorbing, dye sound track, of at least one 1-hydroxy-2-N-(5-alkyl-thiazol-2-yl)-naphthamide coupler that is capable of forming an infrared-absorbing quinone imine dye by reaction with an oxidized aromatic primary amino developing agent, the thiazol-2-yl group of said naphthamide couplers bearing a 4-paraphenyl group or a 4-para-$C_1$-$C_4$alkylphenyl group, the hydrogen atoms of said $C_1$-$C_4$alkoxy or $C_1$-$C_4$alkyl being unsubstituted or at least one of them having been substituted by a halogen atom.

1-Hydroxy-2-N-(5-alkyl-thiazol-2-yl)-naphthamide couplers, which can be prepared very simply and are very interesting from an economical standpoint, are those corresponding to the following general formula:

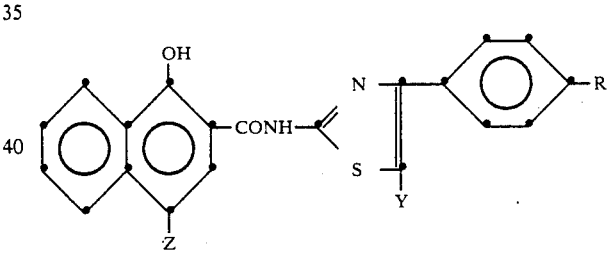

wherein represent:

R—a $C_1$-$C_4$alkoxy group e.g. methoxy and ethoxy, a $C_1$-$C_4$alkyl group e.g. methyl, or a $C_1$-$C_4$alkoxy group or $C_1$-$C_4$alkyl group wherein at least one of the hydrogen atoms has been replaced by a halogen atom such as fluorine e.g. difluoromethoxy;

Y—an alkyl group having at least 8 carbon atoms e.g. tetradecyl, which renders the coupler fast to diffusion in hydrophilic colloid media;

Z—hydrogen or a substituent, e.g. a chlorine atom, that splits off during the coupling reaction, thus conferring 2-equivalent character to the coupler.

In addition to chlorine, other interesting substituents that may confer 2-equivalent character to the naphthamide couplers of the present invention are e.g. an acyloxy group, an alkoxy group, an aryloxy group, a heterocycloxy group, an alkylthio group, an arylthio group e.g. phenylthio and carboxyphenylthio, an alkylsulphonyl group, an arylsulphonyl group, an alkylsulphinyl group, an arylsulphinyl group, an alkyl- or aryl-substituted carbonylmethoxy group, an alkoxy- or aryloxy-substituted carbonylmethoxy group, and a heterocyclic thio group such as a tetrazolylthio group.

The present invention provides a photographic element comprising a support and a plurality of photosensitive silver halide emulsion layers for forming a multicolour photographic dye image and an integral, infrared-absorbing, dye sound track, one of said photosensitive silver halide emulsion layers or a non-photosensitive hydrophilic colloid layer in water-permeable relationship therewith, comprising at least one dispersed 1-hydroxy-2-N-(5-alkylthiazol-2-yl)- naphthamide coupler capable of forming an infrared-absorbing quinone imine dye by reaction with an oxidized aromatic primary amino developing agent characterized in that said naphthamide coupler bears on the thiazol-2-yl group a 4-paraC$_1$-C$_4$alkoxyphenyl group or a 4-para-C$_1$-C$_4$alkylphenyl group, the hydrogen atoms of said C$_1$-C$_4$alkoxy or C$_1$-C$_4$alkyl being unsubstituted or at least one of them having been substituted by a halogen atom.

According to one embodiment of the present invention a photographic element is provided, which comprises:
a support,
an image-recording layer pack comprising in any desired sequence at least one image-recording blue-sensitive gelatin silver halide emulsion layer containing at least one yellow image dye-forming coupler, at least one image-recording red-sensitized gelatin silver halide emulsion layer containing at least one cyan image dye-forming coupler, at least one image-recording green-sensitized gelatin silver halide emulsion layer containing at least one magenta image dye-forming coupler, and one or more intermediate layers between said image-recording emulsion layers,
a photosensitive sound-recording gelatin silver halide emulsion layer, and
an antistress layer,
said photosensitive sound-recording layer and/or a non-photosensitive hydrophilic colloid layer in water-permeable relationship therewith comprising said 1-hydroxy-2-N-(5-alkyl-thiazol-2-yl)-naphthamide coupler.

The present invention further also provides infrared-absorbing quinone imine dyes formed by a coupling reaction between an oxidized aromatic primary amino compound and the said 1-hydroxy-2-N-(5-alkylthiazol-2-yl)- naphthamide coupler.

Representative examples of 1-hydroxy-2-N-(5-alkyl-thiazol-2-yl)-naphthamide couplers that can be used in accordance with the present invention are listed in the following Table 1, the symbols used therein referring to the above general formula.

TABLE 1

| Coupler No. | R | Y | Z | Melting point |
| --- | --- | --- | --- | --- |
| 1 | methoxy | tetradecyl | chloro | 138 |
| 2 | ethoxy | tetradecyl | chloro | 150 |
| 3 | difluoromethoxy | tetradecyl | chloro | 143 |
| 4 | methyl | tetradecyl | chloro | 136 |

The novel couplers according to the present invention can be prepared by techniques well known to those skilled in the art e.g. according to the following general reaction scheme by first performing a cyclization reaction of appropriately substituted α-bromo-alkanoylbenzene derivatives with thiourea to form the corresponding 2-aminothiazoles and next to carry out a condensation of phenyl-1-hydroxynaphthoates, which may carry a coupling off substituent in the 4-position, with these 2-aminothiazoles. In the following general reaction scheme, R has the significance as defined under the above general formula.

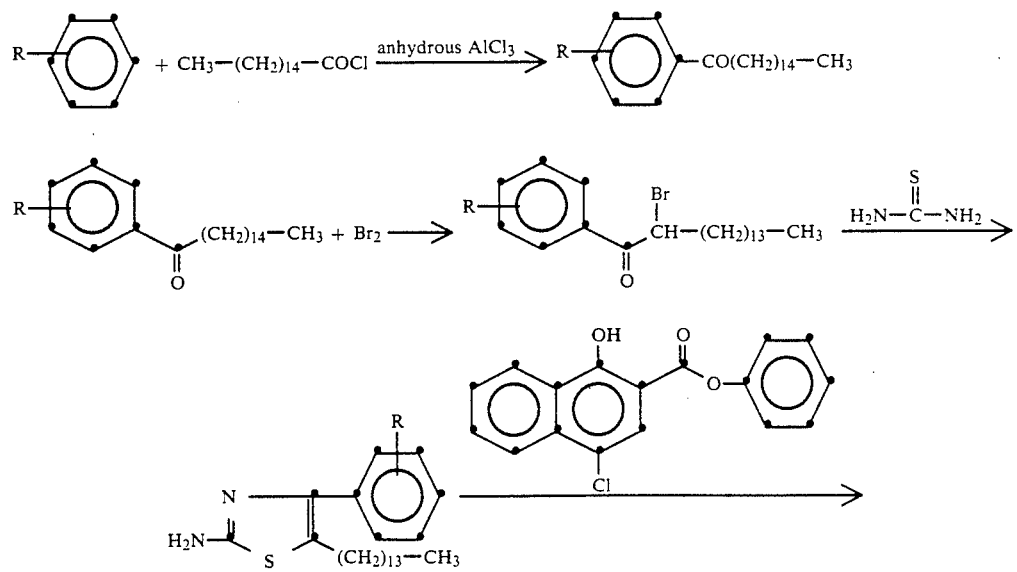

-continued

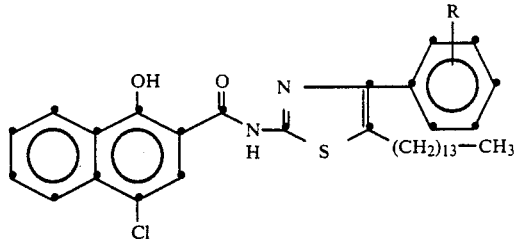

According this reaction scheme the 1-hydroxy-2-N-(5-alkyl-thiazol-2-yl)-naphthamide couplers corresponding to the above general formula can be prepared very simply and very economically.

It was surprising to find that among the many substituents on the thiazol-2-yl group, which have been studied, only the above-specified alkoxyphenyl and alkylphenyl substituents of the couplers of the present invention made it possible to form quinone imine dyes having infrared absorption characteristics significantly better than those of the known couplers not containing the said specific substituents. The infrared absorption range of the quinone imine dyes formed in accordance with the present invention extends from the red region at about 600 nm to well into the infrared region at about 1000 nm. This absorption range consequently covers the entire sensitivity range of the S-1 photocells. Moreover, the broadening of the absorption peak with increasing colour density is considerable and progressive. The density values obtained with the quinone imine dyes formed in accordance with the present invention are much more favourable than those obtained with the known quinone imine dyes. In general, the maximum dye density of these quinone imine dyes produced throughout the spectral region of from 750 to 850 nm may exceed 1.5. The signal-to-noise ratio of the dye sound tracks made in accordance with the present invention is better than that of known dye sound tracks. Heat stability tests and dark-fading tests have proved that the heat and light stability of the infrared-absorbing sound track dyes obtained from the couplers used in accordance with the present invention are very good and that the loss in density of the dye tracks during ageing is very low.

The couplers according to the present invention can thus be used advantageously in a hydrophilic colloid layer of colour photographic motion picture elements for forming infrared-absorbing dyes for integral dye sound tracks. The couplers of the present invention can be incorporated successfully into a hydrophilic colloid layer by dissolving them first in at least one water-immiscible, oil-type solvent or oil-former, adding the resulting solution to an aqueous phase containing gelatin and a dispersing agent, passing the mixture through a homogenizing apparatus so that a dispersion of the oily coupler solution in an aqueous medium is formed, mixing the dispersion with a hydrophilic colloid composition e.g. a gelatin silver halide emulsion, and coating the resulting composition in the usual manner to produce a system in which particles of coupler, surrounded by an oily membrane, are distributed throughout the gel matrix. The dissolution of the coupler in the oil-former may be facilitated by the use of an auxiliary low-boiling water-immiscible solvent, which is removed afterwards by evaporation.

The couplers according to the present invention can be dispersed in hydrophilic colloid compositions with the aid of at least one known oil-formers such as an alkyl ester of phthalic acid, e.g. dimethyl phthalate, diethyl phthalate, di-n-butyl phthalate, di-i-amyl phthalate, dihexyl phthalate, diheptyl phthalate, dioctyl phthalate, dinonyl phthalate, didecyl phthalate, n-amyl phthalate, dibutylmonochlorophthalate, butylphthalylbutyl glycolate, 2,4-di-n-amylphenol, 2,4-di-tert-amylphenol, a phosphoric acid acid ester e.g. diphenyl phosphate, triphenyl phosphate, tri-o, m-, or p-cresyl phosphate, o-cresyl diphenyl phosphate, dioctyl phosphate, dioctyl butyl phosphate, tri-n-octyl phosphate, tri-ndecyl phosphate, trixylenyl phosphate, tris-(isopropylphenyl)-phosphate, tributyl phosphate, trihexyl phosphate, trinonyl phosphate, trioleyl phosphate, tris-(butoxyethyl)phosphate, a citric acid ester e.g. O-acetyltriethyl-(or butyl-, hexyl-, octyl-, nonyl-, or decyl)-citrate, a benzoic acid ester e.g. butyl (or hexyl-, heptyl-, octyl-, nonyl-, decyl-, undecyl-, dodecyl-, tridecyl-, tetradecyl-, hexadecyl-, octadecyl-, oleyl-, etc.) benzoate, n-butyl-2-methoxy benzoate, pentyl-o-methyl benzoate, decyl-pmethyl-benzoate, octyl-o-chlorobenzoate, lauryl-p-chlorobenzoate, propyl-2,4-dichlorobenzoate, octyl-2,4-dichlorobenzoate, stearyl-2,4-dichlorobenzoate, oleyl-2,4-dichlorobenzoate, octyl-p-methoxybenzoate, a fatty acid ester e.g. hexadecyl myristate, dibutoxyethyl succinate, dioctyl adipate, dioctyl azelate, decamethylene-1,10-diol diacetate, triacetin, tributyrin, benzyl caprate, pentaerythrite tetracapronate, isosorbide dicaprylate, an amide e.g. N,N-dimethyl lauramide, N,N-diethyl lauramide, N,N,di-n-butyl lauramide, N-butylbenzene sulphonamide, trioctyl trimellitate, a chlorinated paraffin, an aliphatic ester of glycerol and derivatives thereof e.g. glycerol triacetate, ethers e.g. allyl ether, or an oil-former as described in i.a. U.S. Pat. Nos. 2,304,940; 2,322,027; 2,353,262; 2,533,514; 2,801,170; 2,801,171; 2,835,579; 2,852,383; 2,949,360; 3,287,134; 3,554,755; 3,700,454; 3,748,141; 3,767,142; 3,779,765; 3,788,857; 3,837,863; 3,936,303; 4,004,928; 4,075,022; 4,106,940; 4,178,183; 4,233,389; 4,250,251; in UK P 958,441; 1,222,753; 1,272,561; 1,424,454; 1,501,233; 2,027,130; in DE OS 2,432,041; 2,538,889; 2,613,504; 2,629,842; 2,903,681; 2,909,402; 2,932,368; in DE P 1,152,610; in JA P 23233/71; 29461/74; 28693/77; 15127/78; 1521/78, in JA Pat.Publications 34715/77; 82078/75; 26037/76; 27921/76; in BE P 768,585 and 833,202, and in the Research Disclosures 18732 (Nov. 1979) p. 634–38 and 16745 (March 1978) p. 58–59.

The couplers according to the present invention can be dispersed easily in hydrophilic colloid compositions with the aid of at least one high-boiling substantially water-insoluble oilformer of the class of substituted 2-propanols and carboxylic; phosphoric, and phosphonic acid esters thereof as disclosed in U.S. Pat. No. 4,430,422. Among these oil-formers, which can be used in combination with the couplers according to the present invention, the carboxylic acid acid esters and especially the 2-ethylhexanoic acid ester of 1,3-di-n-octyloxy-2-propanol, the myristic acid ester of 1,3-dimethoxy-2-propanol, the 2-ethylhexanoic acid ester of 1-n-butoxy-3-(2'-ethyl)-n-hexyloxy-2-propanol, the myristic acid ester of 1-methoxy-2-pro- panol, and the 2-ethylhexanoic acid ester of 1,3-di-n-hexyloxy-2-propanol offer the best results. The combination of the couplers according to the present invention with these especially identified oil-formers results in additional advantages in that an even higher bathochromic shift as well as a strong oppression of opalescence may be obtained.

The couplers according to the present invention can also be dispersed in hydrophilic colloid compositions with the aid of a combination of at least one of the above-mentioned known oil-formers and at least one of the above-mentioned high-boiling substantially water-insoluble oil-formers of the class of substituted 2-propanols and carboxylic, phosphoric, and phosphonic acid esters thereof.

For dispersing the couplers according to the present invention, the oil-formers, especially those of the class of substituted 2-propanols and carboxylic, phosphoric, and phosphonic acid esters thereof can be used in widely varying concentrations e.g. in amounts ranging from about 0.1 to about 10 parts by weight and preferably from 0.5 to 2 parts by weight relative to the amount of the couplers dispersed therewith. Excellent results were obtained with 0.5 part by weight of the oil-formers relative to 1 part of the couplers of the invention. For instance, very good results were obtained with a fine-grain silver halide sound-recording emulsion comprising per sq. m. an amount of silver that is equivalent with 0.6 g of silver nitrate, 0.8 g of coupler according to the invention, and 0.4 g of preferentially used oil-former.

Inasmuch as the nature and the concentration of the oil-formers may have an influence on the absorption characteristics of the quinone imine dyes obtained from the couplers according to the invention, it may thus be possible to adjust the absorption spectrum of these dyes in a desired sense by establishing the optimum oil-former composition and adjusting the concentration of said preferentially used oil-formers.

It may be useful to combine at least one of the above defined oil-formers with at least one auxiliary solvent that is insoluble or almost insoluble in water and has a boiling point of at most 150° C., such as lower alkyl acetates e.g. methyl acetate, ethyl acetate, n-propyl acetate, isopropyl acetate, butyl acetate, ethyl formiate, methyl propionate, ethyl propionate, carbon tetrachloride, sym-dichloroethylene, trichloroethylene, 1,2-dichloropropane, chloroform, amyl chloride, diethyl carbonate, diethyl ketone; methyl ethyl ketone, methyl-n-propylketone, diethyl ketone, diisopropyl ether, cyclohexane, methylcyclohexane, ligroin, benzene, toluene, xylene, nitromethane. The auxiliary solvent may also be a water-soluble organic solvent such as methanol, ethanol, isopropanol, dimethylsulphoxide, tetrahydrofuran, N-methylpyrrolidone, dioxan, acetone, butyrolactone, ethylene glycol, ethylene glycol monomethyl ether, ethylene glycol monoethyl ether, ethylene glycol monobutyl ether, diethylene glycol monoethyl ether, diethylene glycol monomethyl ether, glycerol, acetonitrile, formamide, dimethylformamide, tetrahydrothiophene dioxide, or dimethoxyethane. The auxiliary solvent may also be one described in i.a. U.S. Pat. Nos. 2,801,170; 2,801,171; 2,949,360; 2,835,579.

For processing the colour photographic motion picture elements for forming the image dyes as well as the infrared-absorbing dyes for integral dye sound tracks any conventional colour developing agent can be employed. Inasmuch as the colour developing agent will react in oxidized form with i.a. the couplers used in accordance with the present invention, the nature of the particular colour developing agent will, of course, also determine the characteristics of the infrared-absorbing dyes obtained therewith. Colour developing agents that are very well suited for processing the colour photographic motion picture elements comprising the couplers of the present invention are e.g. 2-amino-5-diethylamino-toluene hydrochloride (CD-2), 2-amino-5-[N-ethyl-N-(methylsulphonylamino)-ethyl]aminotoluene sulphate (CD-3), 4-amino-3-methyl-N-ethyl-N(-hydroxyethyl)aniline sulphate (CD-4), and N,N-diethyl-p-phenylene diamine sulphate (TSS).

The colour photographic motion picture elements comprising the couplers of the present invention can be of the positive print film type or of the reversal film type.

Further details on the formation of integral infrared-absorbing sound tracks in photographic elements and on the infrared-absorbing quinone imine dyes obtained therewith as coupling product in a separate layer of such photographic elements during the same processing step as the one wherein the colour image is formed, can be found in U.S. Pat. Nos. 4,178,183; 4,233,389; 4,250,251; 4,430,422 and in the Research Disclosures 18 732 (Nov. 1979) p. 634–638; 15 125 (Nov. 1976) p. 24–25; 13 460 (June 1975) p. 50.

Such sound-recording layer(s) should have a spectral or general sensitivity such that an undesired image is not formed on image-wise exposure of the image-recording layers.

The couplers of the present invention used for forming infrared-absorbing quinone imine dyes can be incorporated into a layer of the sound-recording layer unit making part of a colour photographic motion picture element. Such element may consist e.g. of a sound-recording layer unit comprising at least one sound-recording photosensitive gelatin silver halide emulsion layer coated on top of the image-recording layers.

A common layer composition of a colour photographic motion picture element comprises in order of sequence : a film support, the blue-sensitive silver halide emulsion layer(s) containing yellow-forming colour coupler(s), optionally (an) intermediate layer(s), the red-sensitized silver halide emulsion layer(s) containing cyan-forming colour coupler(s), optionally (an) intermediate layer(s), and the green-sensitized silver halide emulsion layer(s) containing magenta-forming colour coupler(s). The sound-recording layer(s) can have different locations as specified hereinafter, e.g. they can be coated on top of the green-sensitized layer(s).

Different sound-recording silver halide compositions are possible. For instance, the sound-recording silver halide emulsion is sensitive to ultraviolet radiation alone, or to infrared radiation, or to radiation of the spectral region between 470 and 500 nm. What is important is that during the image exposure of the colour element the sound-recording layer does not respond. In these cases the sound-recording layer can be coated directly on the uppermost green-sensitized layer.

According to another alternative the sound-recording layer can be sensitive to the blue spectral region, but to a far less extent than the blue-sensitive layer(s) containing the yellow-forming couplers so that during the image exposure of the colour photographic motion picture element the sound-recording layer does not respond. The blue-sensitive sound-recording layer, which can e.g. be a fine-grain silver chlorobromide emulsion sensitive in the spectral range from 400 to 470 nm, may comprise a cyan-forming coupler in addition to the coupler forming an infrared-absorbing dye. When an additional cyan-forming coupler is used, the reaction with oxidized developer leads to the formation of a cyan dye in addition to the infrared-absorbing dye according to the invention. Cyan dyes are known to absorb also in the lower infrared region. The combined infrared absorption of both dyes thus increases the infrared absorption range and the density.

Likewise according to a further alternative the sound-recording layer can be sensitive to the green spectral region, but to a far less extent than the green-sensitized layer so that during the image exposure of the colour photographic motion picture element the sound-recording layer does not respond.

According to a further alternative the sound-recording layer can be sensitive to the red spectral region.

The sound-recording layer can be sensitive to both the red and green spectral regions, but to a far less extent than the image-recording red-sensitized and green-sensitized layer(s) so that during the image exposure of the colour photographic motion picture element the sound-recording layer does not respond.

According to all these above-mentioned embodiments the sound-recording layer contains one or more couplers for forming infrared-absorbing dye sound tracks.

According to a further embodiment the colour photographic motion picture element comprises in order of sequence a film support, the blue-sensitive silver halide emulsion layer(s) containing yellow-forming colour coupler(s), optionally (an) intermediate layer(s), the red-sensitized silver halide emulsion layer(s) containing cyan-forming colour coupler(s), optionally (an) intermediate layer(s), the sound-recording silver halide emulsion layer(s) containing coupler(s) forming infrared-absorbing dye(s) in accordance with the invention, optionally (an) intermediate layer(s), the green-sensitized silver halide emulsion layer(s) containing magenta-forming colour couplers, and if desired (an) antistress layer(s). According to this embodiment the sound-recording silver halide emulsion layer(s) containing coupler(s) forming infrared-absorbing dye(s) in accordance with the invention is (are) sensitive in the blue spectral region from 400 to 470 nm, but is (are) far less sensitive than the blue-sensitive silver halide emulsion layer(s), and it (they) may contain in addition to the coupler(s) forming infrared-absorbing dye(s) (a) cyan-forming colour coupler(s) as already described above. The silver halide of this (these) sound-recording emulsion layer(s) may be silver chloride or chlorobromide, preferably fine-grain silver chloride comprising 0–40 mol % bromide and 0–5 mol % iodide.

According to a different embodiment the colour photographic motion picture element does not encompass a separate sound-recording layer containing a coupler that is capable of forming infrared-absorbing dyes. Instead thereof the latter couplers can be incorporated e.g. together with magenta-forming coupler(s) into the green-sensitized layer(s). However, the coupling speed of the magenta-forming couplers should then substantially exceed the coupling speed of the couplers forming the sound track dyes, so that in case of a normal image-wise exposure, the latter couplers, which are slow-coupling, cannot be affected as a result of insufficient amounts of oxidized developer. During the intensive sound track exposure both kinds of couplers respond and form their respective dyes, but the S-1 photocells only react to the infrared density obtained. Alternatively, the couplers that are capable of forming infrared-absorbing dyes can be incorporated together with the cyan image-forming coupler(s) into the red-sensitized layer(s). During the intensive sound track exposure both kinds of couplers respond and form their respective dyes, but the S-1 photocells again only react to the infrared density obtained.

In all above-mentioned embodiments the uppermost emulsion layer may, of course, be protected by (an) antistress layer(s).

Further details on layer structures of colour photographic motion picture elements can be found in U.S. Pat. Nos. 3,705,799 - 3,705,801 - 3,737,312, and 4,208,210; in DE-OS 2,302,661; in UK-P 1,411,311 - 1,429,108, and in the Research Disclosure 18 732 (November 79) p. 634–38.

Although in the making of dispersions of the couplers of the invention in hydrophilic colloid compositions gelatin is favoured as hydrophilic colloid, other water-soluble colloidal substances or mixtures of these can be used too e.g. colloidal albumin, starch, zein, alginic acid and derivatives thereof, such as salts, esters, and amides, casein, cellulose derivatives such as carboxymethyl cellulose, synthetic hydrophilic colloids such as polyvinyl alcohol, poly-N-vinyl pyrrolidone, anionic polyurethans, copolymers of acrylic esters, acrylonitrile, and acrylamides, etc.

During the manufacture of the colour photographic silver halide motion picture element according to the invention, the couplers corresponding to the above general formula can be incorporated in the presence of at least one of the above defined oil-formers into the coating composition of the silver halide emulsion layer(s) or other colloid layer(s) in water-permeable relationship therewith according to any technique known by those skilled in the art of incorporating couplers, into colloid compositions. For more details about particularly suitable techniques that can be employed for dispersing the couplers of the invention into hydrophilic colloid compositions there can be referred to U.S. Pat. Nos. 2,304,939; 2,304,940; 2,322,027; 2,801,170; 2,801,171; and 2,949,360.

The couplers of the invention can be dispersed in the presence of a surface-active agent or dispersing aid. The surface-active agent used may be of the ionic, non-ionic or amphoteric type. Examples of suitable ionic surface-active agents are the sodium salt of oleylmethyltauride, sodium stearate, 2-heptadecyl-benzimidazole-5-sulphonic acid sodium salt, sodium sulphates of aliphatic alcohols containing more than 5 carbon atoms per molecule, e.g. 2-methylhexanol sodium sulphate; the sodium salt of di-isooctyl ester of sulphonated succinic acid, sodium dodecyl sulphate and p-dodecylbenzene sulphonic acid sodium salt. Examples of suitable non-ionic surface-active agents are saponine, condensation products of ethylene oxide and alkyl phenols, e.g. p-octylphenol and p-isononyl phenol and phenylethylene glycol oleate. Other examples of anionic and non-ionic surface-active agents can be found in UK P 1,460,894.

A survey of surface-active agents, representatives of which can be used in dispersing the couplers of the present invention, was made by Gerhard Gawalek in "Wash- und Netzmittel" Akademieverlag, Berlin (1962).

It is also possible to use mixtures of anionic and nonionic surface-active agents as described e.g. in UK P 1,460,894.

Other interesting surface-active agents that can be used in dispersing the couplers of the invention are the short-chain fluorine-containing surface-active agents disclosed in U.S. Pat. No. 4,292,402.

The photosensitive silver halide emulsions used in the making of colour photographic motion picture elements according to the present invention can be sensitized chemically as well as optically. They can be sensitized chemically by carrying out the ripening in the presence of small amounts of sulphur-containing compounds such as allyl thiocyanate, allyl thiourea, or sodium thiosulphate. The emulsions can also be sensitized by means of reducing agents e.g. tin compounds as described in FR P 1,146,955 and in BE P 568,687, imino-aminomethane sulphinic acid compounds as described in UK P 789,823 and small amounts of noble metal compounds such as gold, platinum, palladium, iridium, ruthenium, and rhodium compounds. They can be sensitized optically by means of cyanine and merocyanine dyes.

The emulsions can also comprise compounds that sensitize the emulsions by development acceleration e.g. compounds of the polyoxyalkylene type such as alkylene oxide condensation products as described i.a. in U.S. Pat. No. 2,531,832 - 2,533,990, in UK P 920,637; 940,051; 945,340; 991,608 and 1,091,705, onium derivatives of amino-N-oxides as described in UK P 1,121,696, and thioethers as described in U.S. Pat. No. 4,292,400. Further, the emulsions may comprise stabilizers e.g. heterocyclic nitrogen-containing thioxo compounds such as benzothiazoline-2-thione and 1-phenyl-2-tetrazoline-5-thione and compounds of the hydroxytriazolopyrimidine type. They can also be stabilized with an aromatic or heterocyclic mercapto compound as described in the UK PA 39457/80 or with mercury compounds such as the mercury compounds described in BE P 524,121; 677,337, and in the UK P 1,173,609.

The hydrophilic colloid layers, in particular the photosensitive emulsions layers, making part of the colour photographic motion picture elements of the present invention may be hardened, if desired, with the aid of known hardening agents. Particularly interesting hardening results were obtained with hardening agents corresponding to the following general formula:

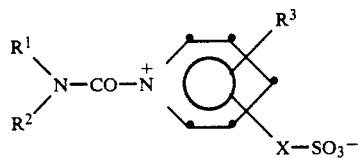

wherein:
each of $R^1$ and $R^2$ (same or different) represent hydrogen, a $C^1$-$C^3$ alkyl group, an aryl group e.g. phenyl, an aryl group substituted with a lower alkyl group or with halogen e.g. phenyl substituted with methyl, ethyl, chloro, or bromo, an aralkyl group e.g. benzyl, an aralkyl group substituted with a lower alkyl group or with halogen, or $R^1$ and $R^2$ together represent the atoms necessary to complete a saturated heterocyclic group, preferably morpholino or piperidino, said saturated heterocyclic group optionally being substituted with a lower alkyl group or with halogen e.g. methyl, ethyl, chloro, or bromo, $R^3$ hydrogen, methyl, or ethyl, and X a chemical bond or a $C_1$-$C_3$ group e.g. methylene, ethylene, or propylene.

The photosensitive emulsions containing the couplers of the invention may also comprise any other kind of ingredient such as those described for such emulsions in Research Disclosure no. 17,643 of December 1978.

The emulsions can be coated on a wide variety of photographic emulsion supports. Typical supports include cellulose ester film, polyvinylacetal film, polystyrene film, polyethylene terephthalate film and related films or resinous materials.

The infrared-absorbing dye sound tracks produced in the colour photographic motion picture elements of the present invention are equal in fidelity with known silver sound tracks. No higher gain is required to achieve comparable decibel output, since the dye sound tracks produced in accordance with the invention—unlike known dye sound tracks—have a maximum density that is of substantially the same value as that of silver sound tracks.

The infrared-absorbing quinone imine dyes formed by a coupling reaction of 1-hydroxy-2-N-(5-alkylthiazol-2-yl)-naphthamide couplers according to the present invention with an oxidized aromatic primary amino compound can be used also as filter dyes in non-photographic materials such as in glass or synthetic resin materials e.g. in window glass as commonly used in shop and office windows for filtering the sun rays. It is obvious that the infrared-absorbing dyes obtained in accordance with the invention may find other interesting applications.

The following examples illustrate the present invention.

EXAMPLE 1

Samples of colour photographic motion picture elements were made, all the samples being identical except for the composition of their sound-recording layer. The difference in the composition of the sound-recording layers only referred to the nature of the coupler and the oil-former used therein. The samples had the following layer sequence:
 black antihalation layer
 transparent film support
 subbing layer
 image-recording blue-sensitive gelatin silver halide emulsion layer containing a yellow image dye-forming coupler
 gelatin intermediate layer
 image-recording red-sensitized gelatin silver halide emulsion layer containing a cyan image dye-forming coupler
 sound-recording chlorobromide emulsion layer sensitive in the blue spectral region from 400 to 470 nm and comprising silver in an amount equivalent to 0.6 g of silver nitrate per sq. m., 1.5 g/sq. m. of gelatin and 0.75 g/sq. m. of coupler, as defined in Table 2, dispersed with the aid of an equal weight of oil-former, also defined in Table 2 hereinafter
 image-recording green-sensitized gelatin silver halide emulsion layer containing a magenta image dye-forming coupler
 antistress layer.

The couplers and oil-formers used in the sound-recording layer of the samples are identified in the following Table 2. The comparison A is 1-hydroxy-2-N-(4-phenyl-5-thiazol-2-yl)-naphthamide, which is the 4-equivalent coupler described in Example 1 of U.S. Pat. No. 4,178,183, and comparison B has the same structure as comparison A except that it is 2-equivalent and as a consequence carries a coupling off group, which in the present case is a chloro substituent at the 4-position of the naphthamide ring system. Couplers 1, 2, and 4 are couplers according to the present invention, identified in Table 1. In the same table reference is made also to the accompanying FIGS. 1 to 8, which show a density versus wavelength (in nm) plot obtained from the measurement on the sound track quinone imine dye formed as described hereinafter.

TABLE 2

| Coupler | Oil-former | refer to FIG. No. |
|---|---|---|
| Comparison A | dibutyl phthalate | 1 |
| Comparison B | dibutyl phthalate | 2 |
| Coupler 1 | dibutyl phthalate | 3 |
| Coupler 1 | 1,3-dimethoxy-2-propanol myristic ester | 4 |
| Coupler 1 | 1,3-di-n-octyloxy-2-propanol 2-ethylhexanoic ester | 5 |
| Coupler 1 | 1-n-butoxy-3-(2'-ethyl)-n-hexyloxy-2-propanol 2-ethylhexanoic ester | 6 |
| Coupler 2 | 1,3-di-n-octyloxy-2-propanol 2-ethylhexanoic ester | 7 |
| Coupler 4 | 1,3-di-n-octyloxy-2-propanol 2-ethylhexanoic ester | 8 |

All samples were exposed similarly to white light having a colour temperature of 3200° K., to be recorded in the image-recording layers and then exposed again in the sound track area to light so as to affect the sound-recording layer.

The exposed samples were then processed as described hereinafter, no special selective treatment being given to the sound-recording layer. The processing was as follows:

The samples were rinsed for 15 s in a prebath at 27° C. having the following composition:

| water | 800 ml |
|---|---|
| borax | 20 g |
| anhydrous sodium sulphate | 100 g |
| sodium hydroxide | 1 g |
| water to make | 1000 ml |
| | (pH 9.25 at 27° C.) |

The black antihalation layer was removed with water at 27° C. Next, the samples were immersed for 3 min in a colour developing bath at 36.7° C. (±0.1) having the following composition:

| water | 800 ml |
|---|---|
| calcium-sequestering agent | 1 ml |
| anhydrous sodium sulphite | 4.35 g |
| 2-amino-5-diethylamino-toluene hydrochloride | 2.95 ml |
| anhydrous sodium carbonate | 17.10 g |
| anhydrous sodium bromide | 1.72 g |
| 7 N sulphuric acid | 0.62 ml |
| water to make | 1000 ml |
| | (pH 10.53 at 27° C.) |

The samples were then treated with the following stopbath for 40 s at 27° C.:

| water | 900 ml |
|---|---|
| 7 N sulphuric acid | 50 ml |
| water to make | 1000 ml |
| | (pH 0.9 at 27° C.) |

The samples were then bleached in the following bath for 1 min at 27° C.:

| water | 900 ml |
|---|---|
| anhydrous potassium hexacyanoferrate (III) | 30 g |
| anhydrous sodium bromide | 17 g |
| water to make | 1000 ml |
| | (pH 6.5 at 27° C.) |

The bleached samples were rinsed in water for 40 s at 27° C. and nest immersed in the following fixing bath for 40 s at 27° C.:

| water | 800 ml |
|---|---|
| 58% aqueous solution of ammonium thiosulphate | 100 ml |
| anhydrous sodium sulphite | 2.50 g |
| anhydrous sodium hydrogen sulphite | 10.30 g |
| water to make | 1000 ml |
| | (pH 5.8 at 27° C.) |

Finally, the samples were rinsed for 1 min in water at 27° C., immersed for 10 s in the following stabilizing bath at 27° C., and allowed to dry:

| water | 900 ml |
|---|---|
| 37.5% aqueous solution of formaldehyde | 15 ml |
| stabilizer additive | 0.14 ml |
| water to make | 1000 ml. |

In consequence of the high density values obtained in the sound tracks, the signal to noise ratio of the dye sound tracks made in accordance with the present invention exceeds that of known dye sound tracks.

Comparable results were obtained with the other couplers of the present invention, which are identified in Table 1 hereinbefore given.

As a consequence of these higher standards reached with the couplers of the present invention, it is possible to use an image- and sound-recording colour photographic motion picture element in which the sound record is processed simultaneously with the image record using the same baths, the sound record entirely consisting of an infrared-absorbing quinone imine dye as described above.

Dark-fading tests of the quinone imine dyes obtained in accordance with the present invention proved that their heat and light stability was excellent and that the loss in density during ageing was very low.

Alternatively, the samples, instead of being bleached with the above hexacyanoferrate (III) bleach bath, could be bleached also with persulphate-based baths by first treating them with the following accelerator bath:

| water | 900 ml |
|---|---|
| anhydrous sodium metabisulphite | 3.3 g |
| glacial acetic acid | 5.0 ml |
| persulphate bleach accelerator | 3.3 g |
| ethylene diamine tetraacetic acid tetrasodium salt | 0.5 g |

-continued

| | |
|---|---|
| water to make | 1000 ml |
| | (pH 4.0 at 27° C.) | and next with the following bleach bath:

| | |
|---|---|
| water | 850 ml |
| chlorine scavenger | 0.35 g |
| sodium persulphate | 33 g |
| sodium chloride | 15 g |
| anhydrous sodium dihydrogen phosphate | 7.0 g |
| 85% phosphoric acid | 2.5 ml |
| water to make | 1000 ml |
| | (pH 2.3 at 27° C.) |

In comparison with the known processing system for forming a silver-based sound track, the above described processing method comprising a bleaching step with the above-described persulphate bleach bath offers an important advantage in that it. does not include a second development and requires but one fixing step.

An even further simplification of the above described processing can be realized by using a bleach-fixing (blix) bath. In that case the processing sequence can be reduced to a treatment with successively the prebath, the colour developing bath, the stopbath, all three as described above, then treatment with the blix-bath having the following composition, rinsing, and treatment with the above described stabilizing bath.

Composition of the blix bath:

| | |
|---|---|
| water | 700 ml |
| sodium sulphite | 10 g |
| mercaptotriazole | 2.5 g |
| ethylene diamine tetraacetic acid tetrasodium salt | 13 g |
| ethylene diamine tetraacetic acid iron salt | 50 g |
| ammonium bromide | 10 g |
| ethylene diamine tetraacetic acid | 5 g |
| ammonium thiosulphate | 150 g |
| water to make | 1000 ml. |
| | (pH 6.3 at 27° C.) |

In order to facilitate evaluation of the quinone imine dye sound tracks formed, samples were prepared of photographic elements as described hereinbefore with the difference that no image-recording layers were coated onto the subbed film support. The samples were exposed through a step wedge having a constant of 0.5, the density steps of which range from density 0.5 at step 1 to density 3 at step 6, to light so as to affect the sound-recording layers. The samples were then processed as described hereinbefore for the multilayer colour photographic motion picture elements containing image-recording layers also.

In the accompanying FIGS. 1 to 8 a plot of density D versus wavelength (in nm) of the quinone imine dye images obtained is shown. The different curves of a plot refer to different consecutive steps of the step wedge, through which the sample was exposed.

Figure 2:
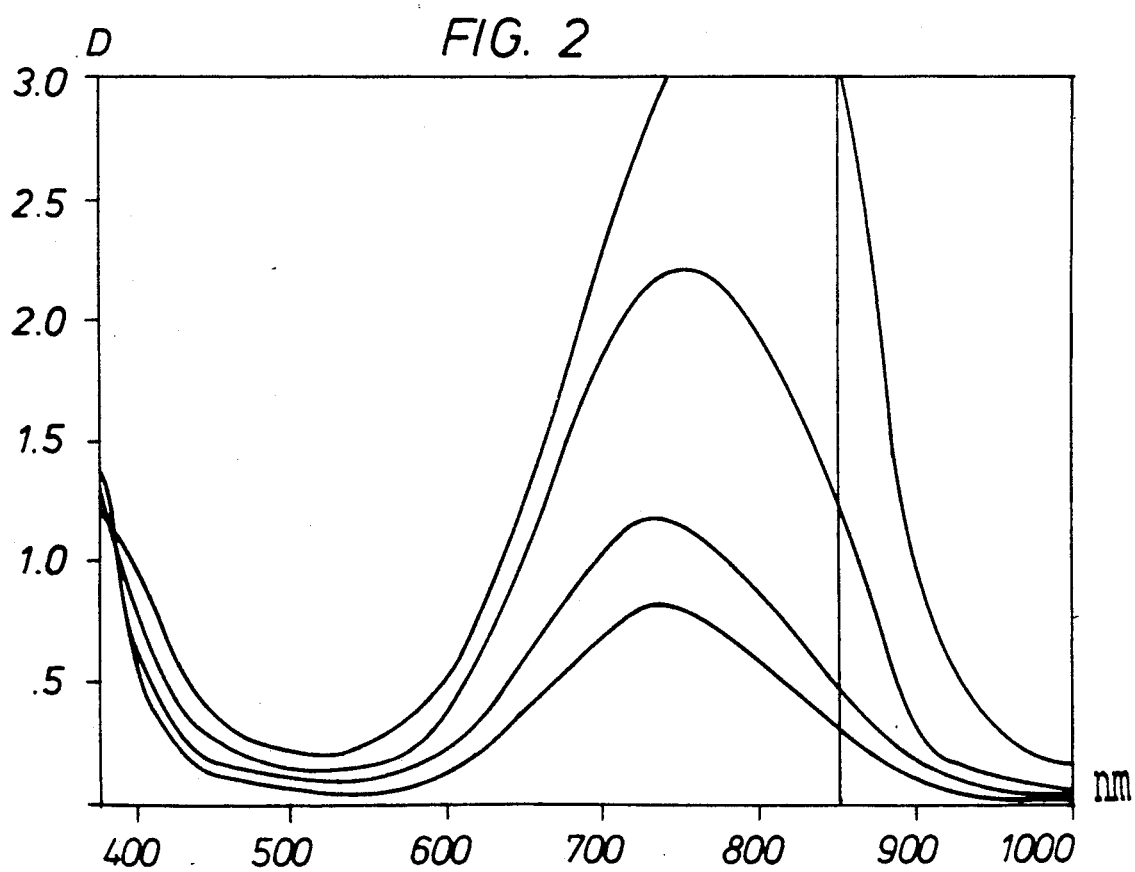
Figure 3:
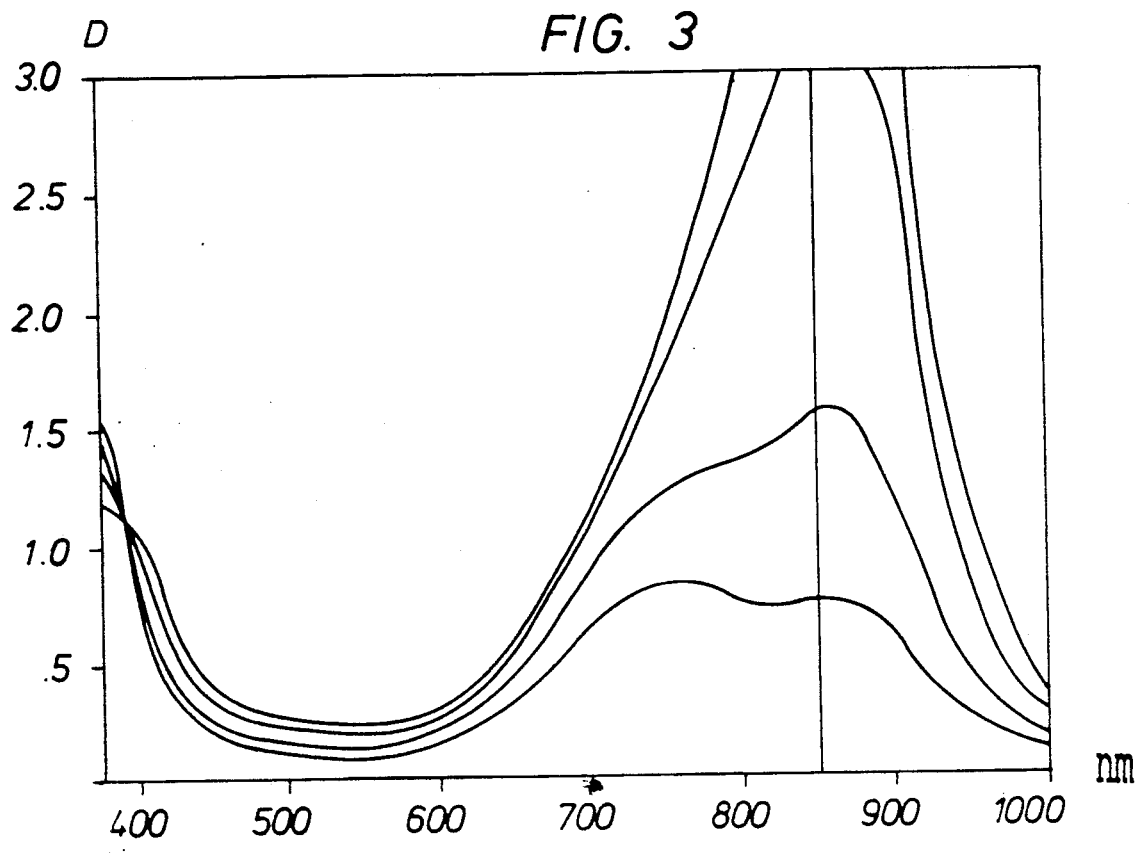
Figure 4:
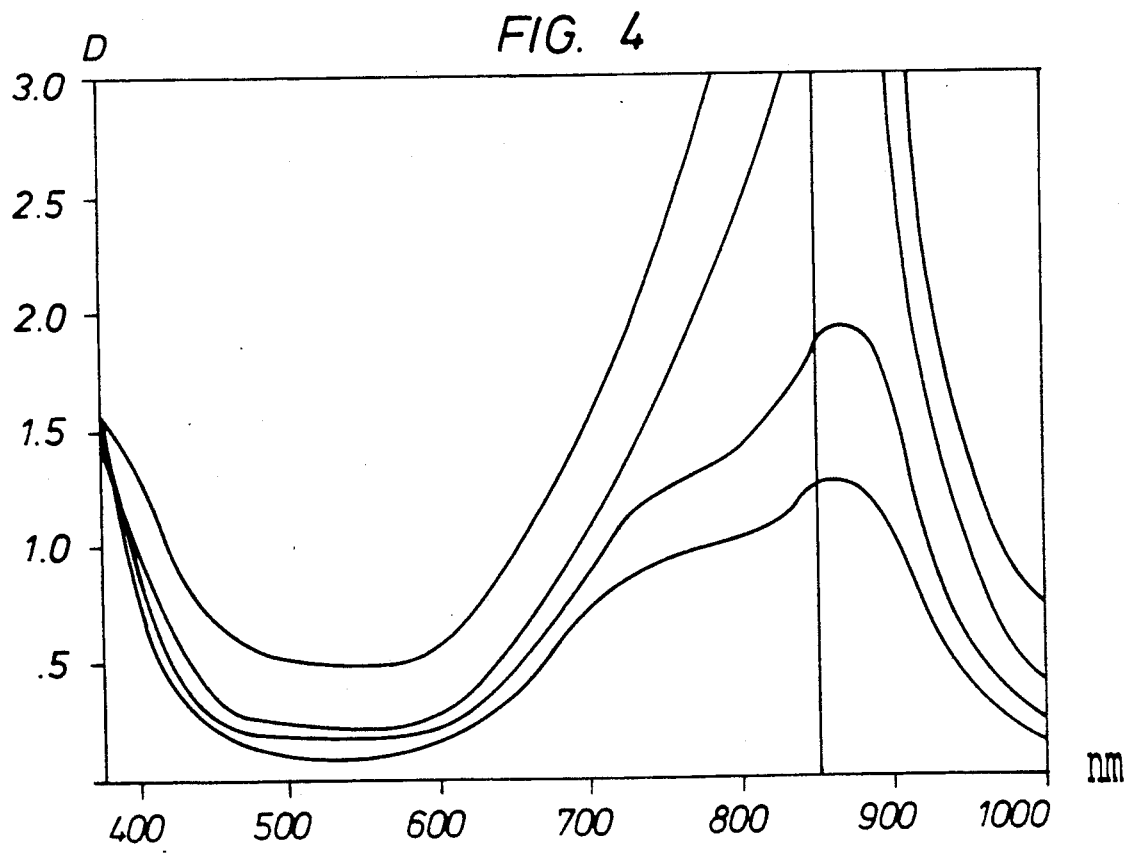
Figure 5:
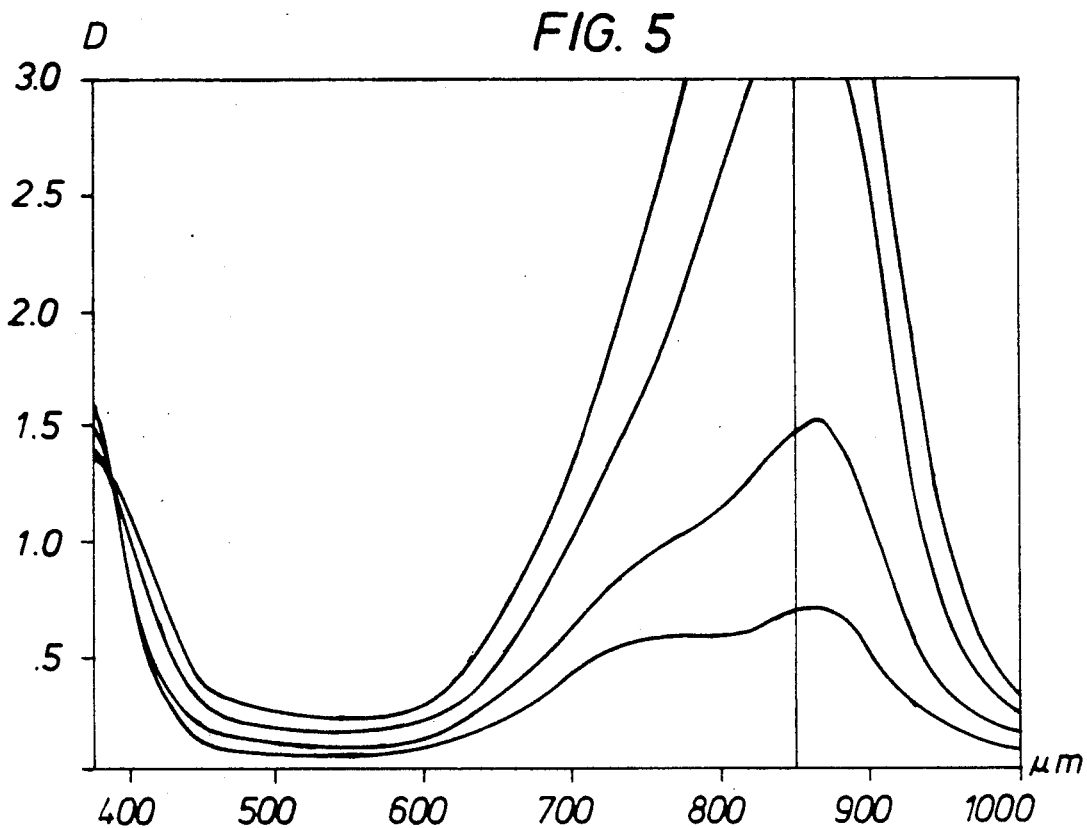
Figure 6:
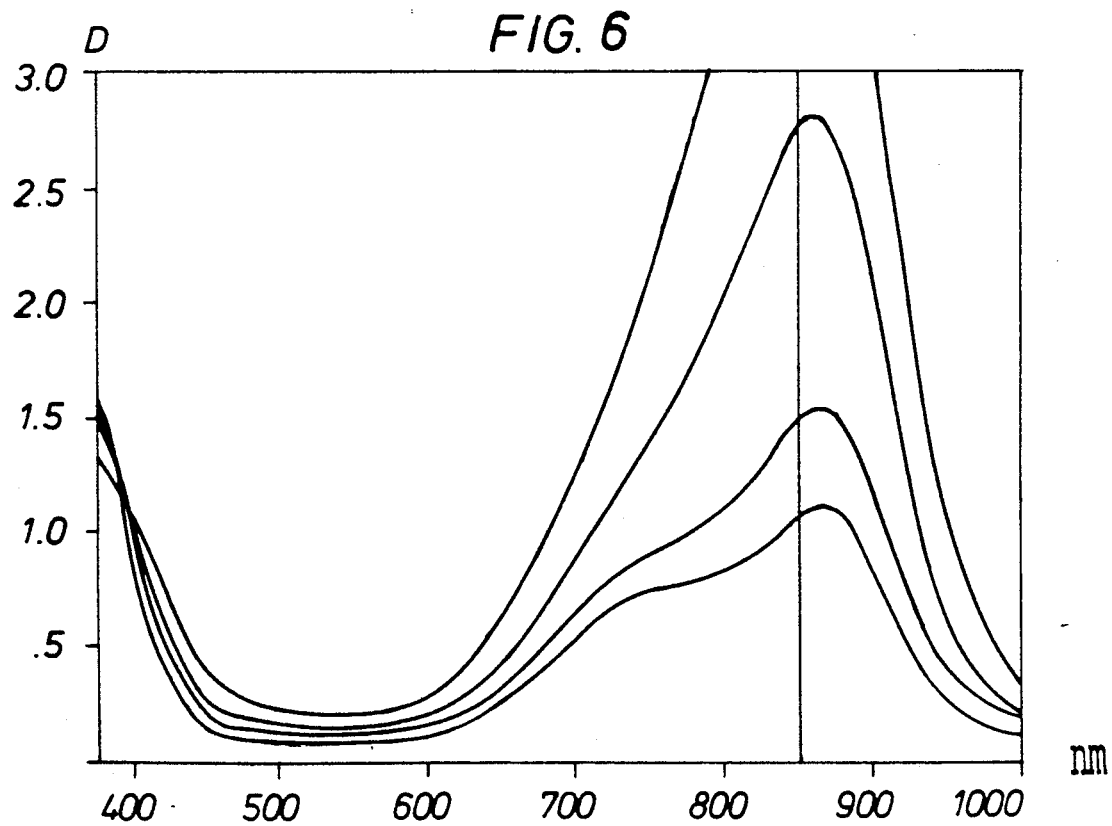
Figure 7:
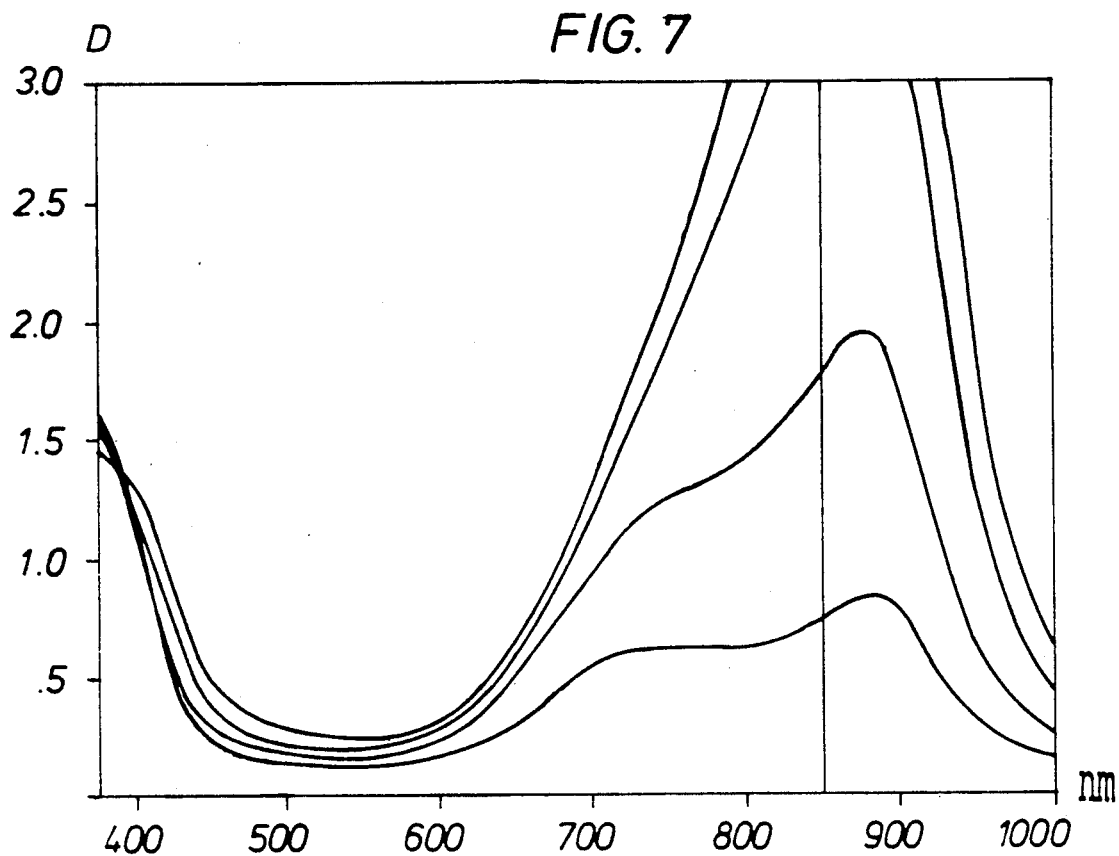
Figure 8:
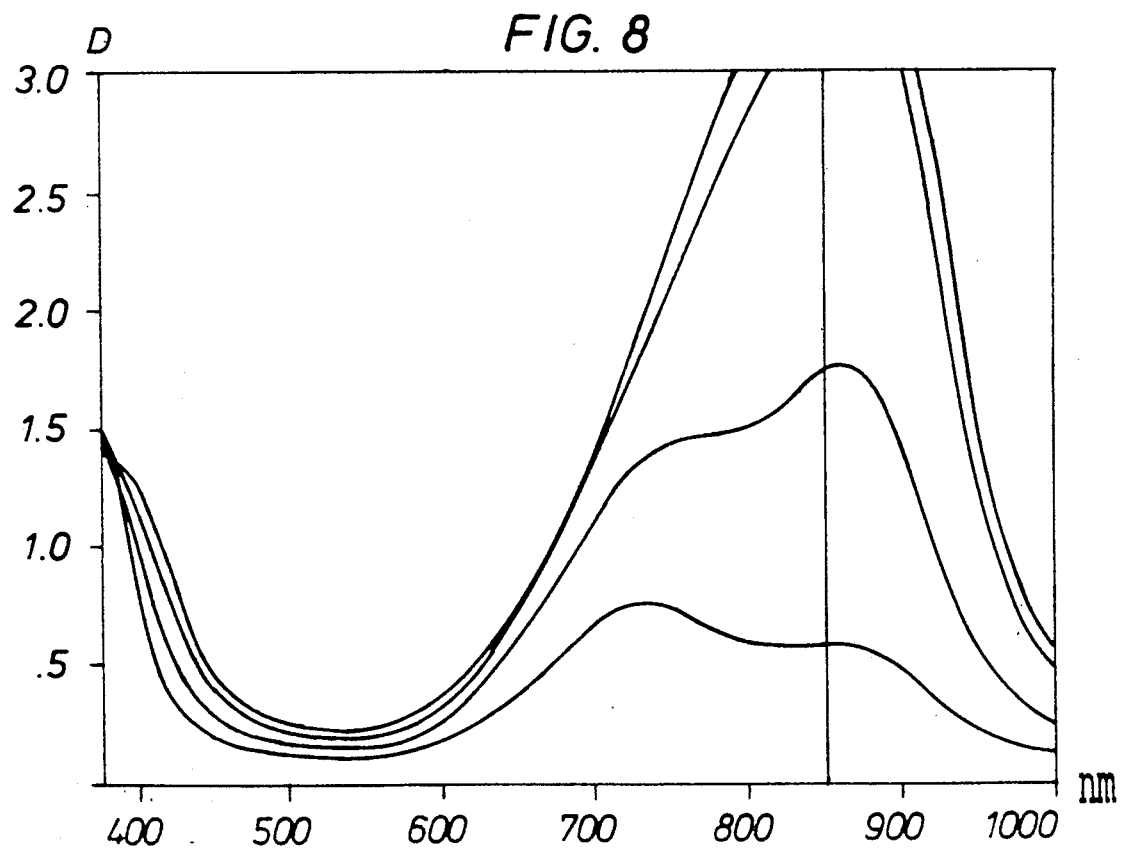
Figure 9:
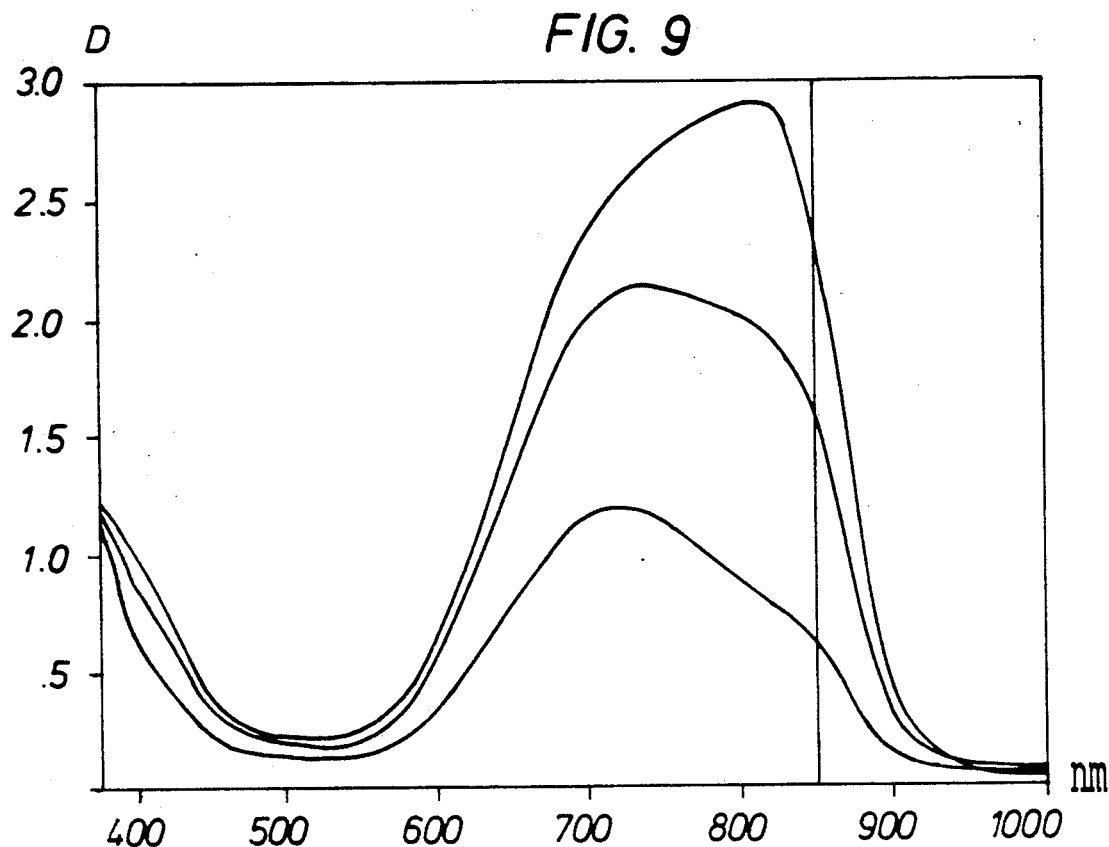

Comparison of the plots shows that the absorption peaks in FIGS. 1 and 2 (comparison couplers A and B respectively dispersed with dibutyl phthalate) range between 740 for the lower curve and 800 nm for the upper curve, whereas the absorption peak in FIG. 3 (coupler 1 dispersed with dibutyl phthalate) ranges between 750 for the lower curve and 860 nm for the upper curve, which is well into the infrared region, and the absorption peaks in FIGS. 4 to 6 (coupler 1 dispersed with the oil-formers indicated in Table 2) and in FIG. 7 (coupler 2) are near 870 nm for both the lower curve and the upper curve, which is even farther into the infrared region.

Further comparison of the plots shows that the absorption ranges of the dyes obtained from comparison couplers A and B in FIGS. 1 and 2 are narrower than those of couplers 1, 2, and 4 in FIGS. 3 to 8, which in the lower curves appear to have two absorption peaks resulting in one broadened composite peak that encompasses the whole sensitivity range of the S-1 photocells.

Comparison of the infrared spectra of the dyes in FIGS. 1 to 8 clearly demonstrates that the values of infrared absorption above 850 nm obtained for the dyes derived from 1, 2, and 4 substantially exceed those of the dyes derived from the comparison couplers. For clarity a reference line has been drawn at wavelength 850 nm in each Figure.

EXAMPLE 2

As referred to in the above Example 1 samples were made of sound-recording layers coated on subbed film supports. The samples were identical, except for the composition of the sound-recording layer. The difference in the composition of the sound-recording layers only referred to the nature of the coupler and the oil-former used therein. These couplers and oil-formers are identified in the following Table 3.

TABLE 3

| Coupler | Oil-former | refer to FIG. No. |
|---|---|---|
| Comparison A | dibutyl phthalate | 9 |
| Coupler 1 | 1,3-dimethoxy-2-propanol myristic ester | 10 |
| Coupler 2 | 1,3-dimethoxy-2-propanol myristic ester | 11 |
| Coupler 4 | 1,3-dimethoxy-2-propanol myristic ester | 12 |

Comparison A is the known coupler identified in Example 1.

All samples were exposed and processed in the same way as described in Example 1, except that instead of the CD-2 colour developing agent of Example 1, the CD-3 colour developing agent 2-amino-5-[N-ethyl-N-(methylsulphonylamino)-]-aminotoluene sulphate was used now. It is to be noted that in CD-3 development a higher exposure dose is required to achieve the same density values as in CD-2 development.

In the accompanying FIGS. 9 to 12 plots of density D versus wavelength (in nm) of the quinone imine dye sound tracks obtained are shown.

Figure 10:
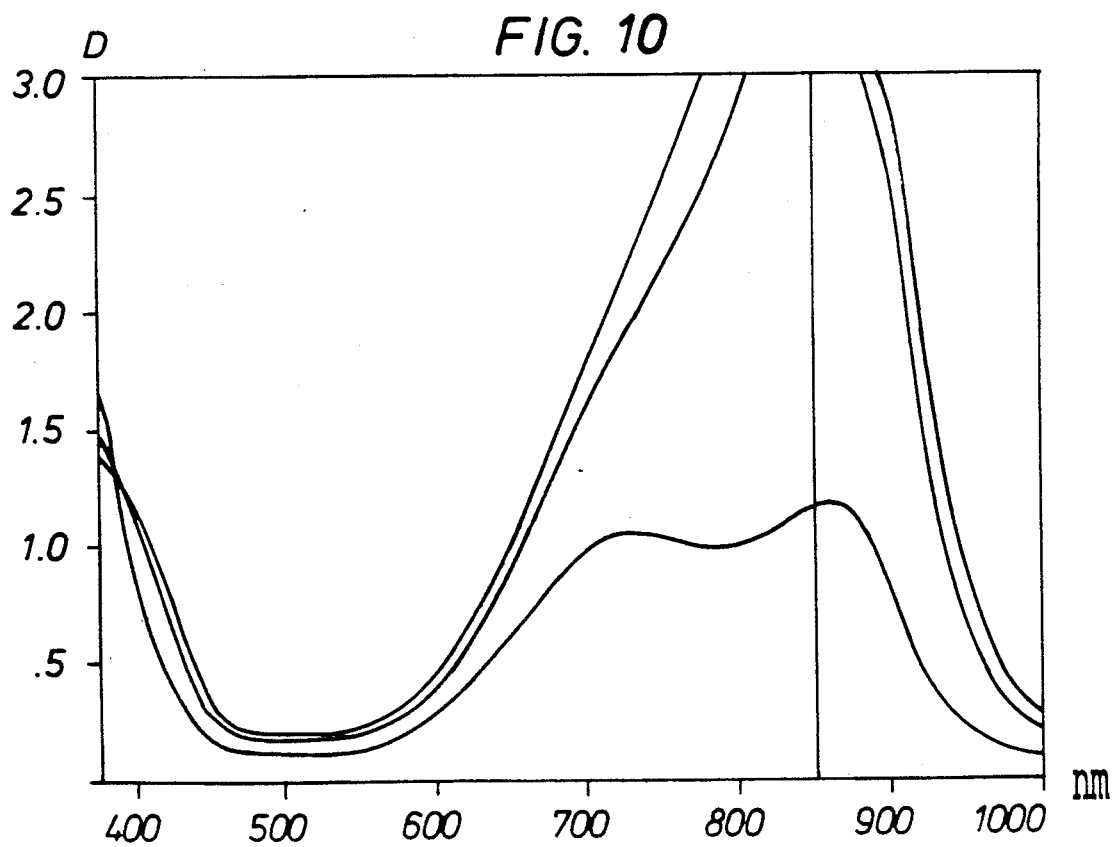
Figure 11:
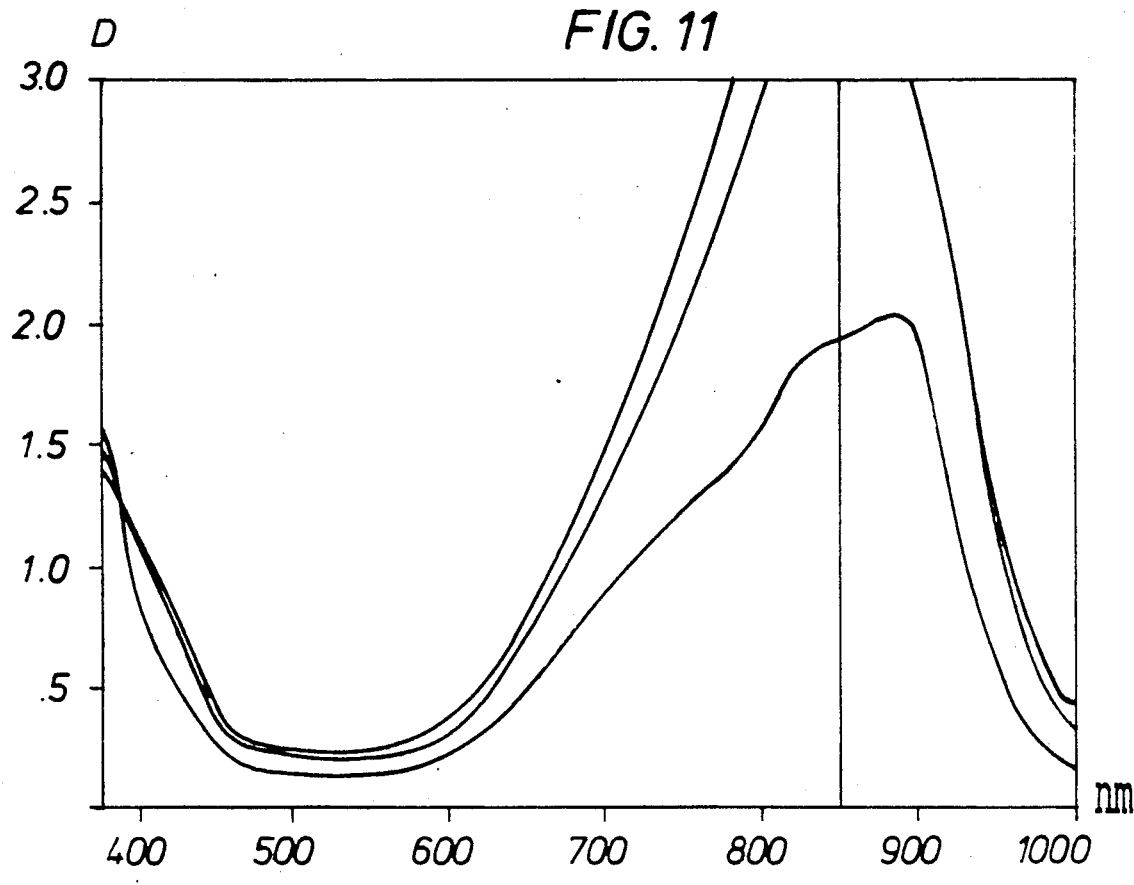
Figure 12:
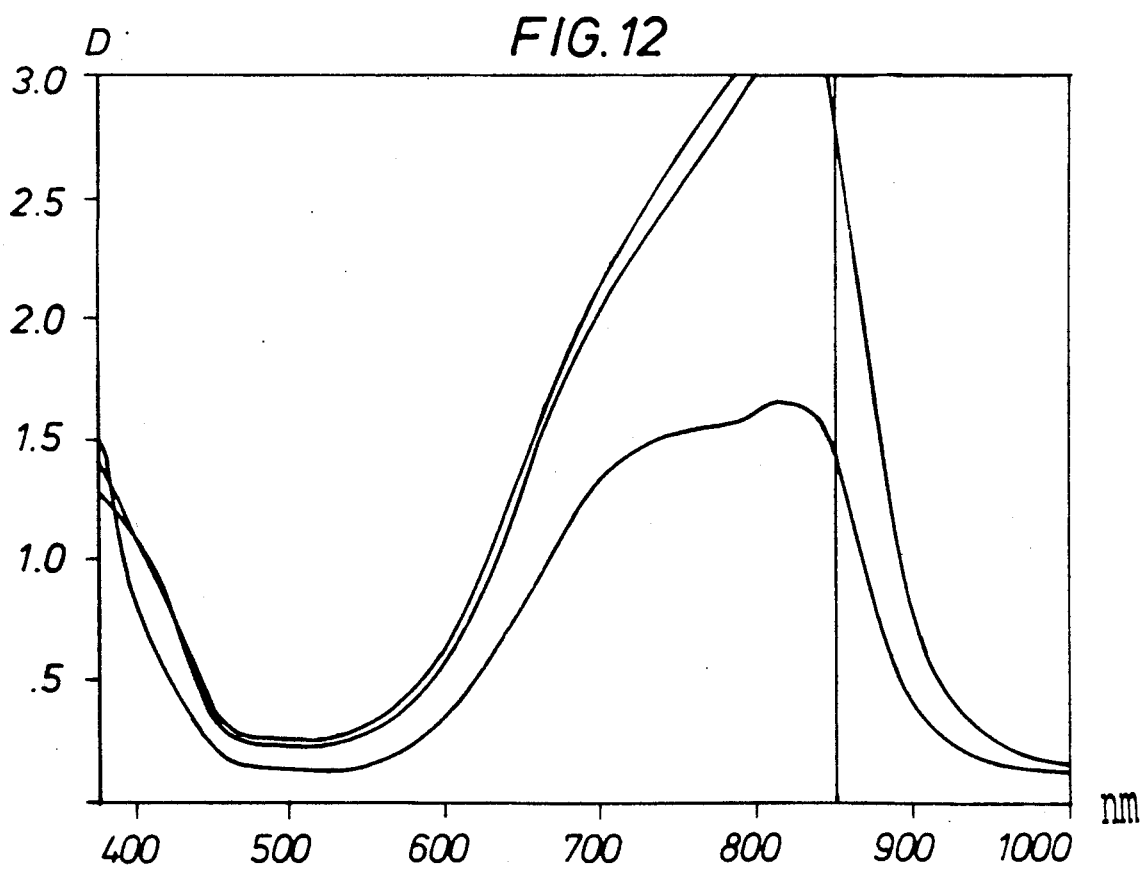

Comparison of these plots learns that the absorption peaks in FIGS. 10 to 12 (couplers 1, 2 and 4 dispersed with the oil-former indicated in Table 3) are closer to the infrared region than those obtained with the known coupler.

Further comparison of the plots also shows that the couplers of the present invention give dyes, which show two absorption peaks resulting in one broadened composite peak that covers the sensitivity range of the S-1 photocells in a better way than the peak obtained from the known dye.

Comparison of the infrared spectra of the dyes in FIGS. 9 to 12 clearly demonstrates that the values of infrared absorption above 850 nm obtained for the dyes derived from couplers 1, 2, and 4 substantially exceed those of the dye derived from the comparison coupler A. For clarity a reference line has been drawn at wavelength 850 nm in each Figure.

In consequence of the high density values obtained, the signal to noise ratio of the dye sound tracks made in accordance with the present invention exceeds that of the known dye sound track.

Comparable results were obtained with the other couplers of the present invention.

We claim:

1. Photographic element comprising a support and a plurality of photosensitive silver halide emulsion layers for forming a multicolour photographic dye image and an integral, infrared-absorbing, dye sound track, one of said photosensitive silver halide emulsion layers or a non-photosensitive hydrophilic colloid layer in water-permeable relationship therewith comprising at least one dispersed 1-hydroxy-2-N-(5-alkylthiazol-2-yl)-naphthamide coupler capable of forming an infrared-absorbing quinone imine dye by reaction with an oxidized aromatic primary amino developing agent, wherein said naphthamide coupler bears on the thiazol-2-yl group a 4-para-$C_1$-$C_4$alkoxyphenyl group or a 4-para-$C_1$-$C_4$-alkylphenyl group, the hydrogen atoms of said $C_1$-$C_4$alkoxy or $C_1$-$C_4$alkyl being unsubstituted or at least one of them having been substituted by a halogen atom.

2. A photographic element according to claim 1, wherein said naphthamide coupler corresponds to the following general formula:

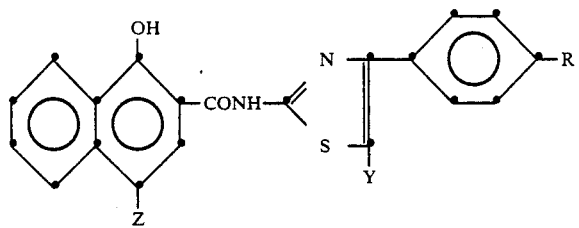

wherein represent:

R—a $C_1$-$C_4$alkoxy group, a $C_1$-$C_4$alkyl group, or a $C_1$-$C_4$alkoxy group or $C_1$-$C_4$alkyl group wherein at least one of the hydrogen atoms has been replaced by a halogen atom;

Y—an alkyl group having at least 8 carbon atoms;

Z—hydrogen or a substituent that splits off during the coupling reaction, thus conferring 2-equivalent character to the coupler.

3. A photographic element according to claim 2, wherein R is methoxy or ethoxy, Y is tetradecyl, and Z is chloro.

4. A photographic element according to claim 1, comprising:
a support,
an image-recording layer pack comprising in any desired sequence at least one image-recording blue-sensitive gelatin silver halide emulsion layer containing at least one yellow image dye-forming coupler at least one image-recording red-sensitized gelatin silver halide emulsion layer containing at least one cyan image dye-forming coupler, at least one image-recording green-sensitized gelatin silver halide emulsion layer containing at least one magenta image dye-forming coupler, and one or more intermediate layers between said image-recording emulsion layers,
a photosensitive sound-recording gelatin silver halide emulsion layer, and
an antistress layer, said photosensitive sound-recording layer and/or a non-photosensitive hydrophilic colloid layer in water-permeable relationship therewith comprising said 1-hydroxy-2-N-(5-alkyl-thiazol-2-yl)-naphthamide coupler.

5. A photographic element according to claim 1, wherein said naphthamide coupler has been dispersed in one of said photosensitive silver halide emulsion layers or in said non-photosensitive hydrophilic colloid layer in water-permeable relation- ship therewith with the aid of at least one high-boiling substantially water-insoluble oil-former.

6. A photographic element according to claim 5, wherein said oil-former is at least one of the class of substituted 2-propanols and carboxylic, phosphoric, and phosphonic acid esters thereof.

7. A photographic element according to claim 6, wherein said oil-former is at least one selected from the group consisting of the 2-ethylhexanoic acid ester of 1,3-di-n-octyloxy-2-propanol, the myristic acid ester of 1,3-dimethoxy-2-propanol, the 2-ethylhexanoic acid ester of 1-n-butoxy-3-(2'-ethyl-n-hexyloxy-2-propanol, the myristic acid ester of 1-methoxy-2-propanol, and the 2-ethylhexanoic acid ester of 1,3-di-n-hexyloxy-2-propanol.

8. A photographic element according to claim 5, wherein said oil-former is used in amounts ranging from 0.5 to 2 parts by weight relative to the amount of said 1-hydroxy-2-N-(5-alkyl-thiazo-2-yl)-naphthamide coupler dispersed therewith.

* * * * *